United States Patent [19]

Nagaya et al.

[11] Patent Number: 4,979,332
[45] Date of Patent: Dec. 25, 1990

[54] CULTURE VESSEL

[75] Inventors: Toshio Nagaya; Shoichi Matsuda, both of Tokyo, Japan

[73] Assignee: Kirin Beer Kabushiki Kaisha, Tokyo, Japan

[21] Appl. No.: 287,101

[22] Filed: Dec. 20, 1988

[30] Foreign Application Priority Data

Jul. 15, 1988 [JP] Japan ............................. 63-93749[U]

[51] Int. Cl.⁵ .............................................. C12M 1/22
[52] U.S. Cl. ......................................... 47/69; 435/296; 435/298
[58] Field of Search ....................... 435/296, 297, 298; 47/69, 17; 220/82 A, 82 R, 508

[56] References Cited

U.S. PATENT DOCUMENTS

| | | | |
|---|---|---|---|
| 2,724,213 | 11/1955 | Weil | 47/69 |
| 2,867,353 | 1/1959 | Botham | 220/82 R |
| 2,971,892 | 2/1961 | Carski | 435/298 |
| 3,995,396 | 12/1976 | Spector | 47/69 |
| 4,044,889 | 8/1977 | Orentreich | 220/82 A |
| 4,285,164 | 8/1981 | Moore | 47/69 |
| 4,508,216 | 4/1985 | Kelman | 220/82 A |
| 4,670,398 | 1/1987 | Song | 435/298 |
| 4,709,657 | 12/1987 | Cothard | 119/5 |
| 4,844,263 | 7/1989 | Hadtke | 206/508 |

FOREIGN PATENT DOCUMENTS

| | | | |
|---|---|---|---|
| 2935691 | 3/1981 | Fed. Rep. of Germany | 220/82 A |
| 477706 | 1/1938 | United Kingdom | 47/69 |

OTHER PUBLICATIONS

Garden Journal, Feb. 1972, p. 22.

Primary Examiner—Henry E. Raduazo
Attorney, Agent, or Firm—Ladas & Parry

[57] ABSTRACT

A culture vessel having a main body and a cover for closing the open top of the main body in which the main body and the cover are made of a thin plastic material having light transmission and heat resistance, the main body has a bottom and a low side wall for accommodating a medium, the side wall has a cover engaging portion formed on the upper end thereof, the cover has a top plate and a vertical side wall, the side wall has a main body engaging portion meshable with the main body formed on the lower end thereof, and lenses for observing, at the side wall, the interior of the vessel in a magnified image are provided on the side wall of the cover.

7 Claims, 4 Drawing Sheets

CULTURE VESSEL

BACKGROUND OF THE INVENTION

This invention relates to a culture vessel for use in culturing plants.

Recently the so-called culture in which bacteria, tissue cells and the like are divided and propagated, is popular. Specifically the culture of cells, which is called tissue culture, cultivates cell groups or tissue pieces. This culture requires media, and various vessels are used to contain the media.

An exemplary vessel for this purpose is a triangular flask of transparent glass as shown in FIG. 12. A medium (b) is put into the flask, and then tissue pieces are placed on the medium. For the prevention of the intrusion of bacteria into the flask, the flask is covered by aluminium foil (c) as shown in FIG. 12(A), or is filled with a cotton plug (d) as shown in FIG. 12(B) or with a silicone plug (e) as shown in FIG. 12(C).

In addition, as shown in FIG. 13, another exemplary vessel is a deep rectangular sectional box (f) of a thick plastic with a shallow cover (g). A medium is put into the box (f), and then tissue pieces are placed on the medium to be cultivated.

However, the above-described conventional triangular flask (a) has the following problems. That is:

(1) The flask (a) has a small mouth and is deep, and the level of a medium in the flask is accordingly low. When the medium is divided, a pincette, for example, has to be reached deep into the flask down to the level of the medium. When it is not well manipulated, the medium scatters to soil the interior of the flask.

(2) When tiny plant tissue pieces are put in, it is difficult to lay them in the same direction, and the manipulation is not efficient.

(3) When a cultured substance which has grown in the flask is transplanted into another vessel, it has to be picked up from the deep bottom of the flask, and the cultured substance can be easily damaged.

(4) Morphological abnormalities, retarded growth, and lowered ratio of tissues settling and growing tend to take place due to excessive water.

In the case of the flask covered with aluminium foil, when the fluid media contact the aluminium foil, withering takes place from the portions which have contacted the aluminium foil.

Compared with the triangular flask described above, the vessel shown in FIG. 13 is less inconvenient, but as far as it is a deep vessel, it cannot overcome the problems (1) to (3) discussed above. In addition, the box (f) has a double-structure at the upper portion on which a cover (g) is put on. This portion has far less transmission of direct lights (l), which are essential to the growth of plants. Such adversely reduced light transmitting area is an additional drawback to the culture vessel.

Furthermore, the above-described two conventional culture vessels do not allow the culturing states of a substance being cultured therein, its germinating and growing states, presence of contaminations, etc. to be visually observed in detail easily. When the vessels are stacked in a plurality of layers, it is harder to visually observe the interiors of the vessels.

In order to provide the above-described vessels with ventilation plugs, ventilation holes are formed in the covers of the vessels, and the ventilation plugs are filled in the ventilation holes so as to ventilate the interiors of the vessels. However, the problems with these plugs are that when the plugs are subject to the vapor pasteurization, they absorb the vapor and then shrink, depending on their materials, and become inoperative any more as the ventilation plugs, and furthermore the water intrudes into the vessels eventually to affect the plant cells therein. Taking into consideration the above-described problems, this invention has been made, and an object of this invention is to provide a culture vessel which facilitates the manipulation of laying in the vessel a substance to be cultivated, such as plant tissue pieces or others, and which allows its interior to be observed accurately even when a plurality of the vessels are stacked.

SUMMARY OF THE INVENTION

In order to solve the problems of the prior art, this invention provides a culture vessel having a main body, and a cover for closing the open top of the main body, the main body and the cover being made of a thin plastic material having light transmission and heat resistance, the main body having a bottom and a low side wall for accommodating media, the side wall having a cover engaging portion formed on the upper end thereof, the cover having a top plate and vertical side wall, the side wall having a main body engaging portion meshable with the main body formed on the lower end thereof, and on the side wall of the cover there being provided lenses for observing, at the side wall, the interior of the vessel in a magnified image.

In the above-described structure of this invention, a medium is put into the main body of the vessel, tissue pieces of, e.g., a plant, are placed on the medium, and then the cover is put on the main body. However, the vertical cover creates no double structure or the like which obstructs the transmission of the incident lights, which results in good transmission of lights into the vessel. Furthermore, the state of the substance being cultivated in the main body can be observed in detail accurately in a magnified image by the lens formed on the side wall of the cover.

DETAILED DESCRIPTION OF THE INVENTION

Figure 1:
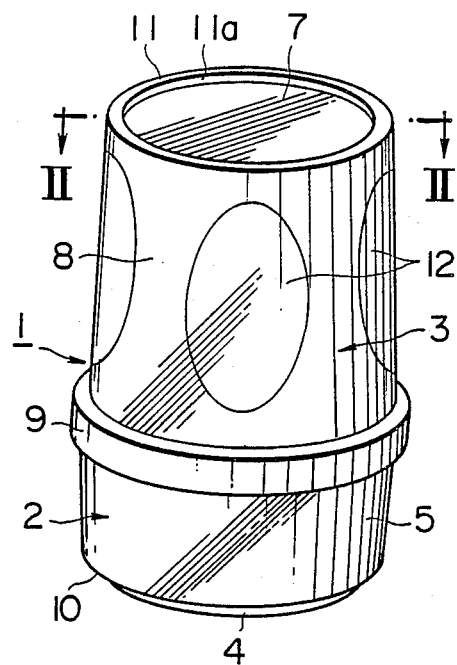
FIG. 1 is a perspective view of one embodiment of the culture vessel according to this invention.

This invention will be explained by means of embodiments illustrated in FIGS. 1 to 11.

The culture vessel 1 according to this invention is substantially cylindrical and comprises a main body 2 and a cover 3 to be put on the open top of the main body 2. The main body 2 and the cover 3 are made of a transparent plastic material, e.g., polycarbonate or others, having such good heat resistance as to bear the pasteurization treatment. The main body 2 comprises a circular bottom 4 and a low side wall 5 rising from the periphery of the circular bottom 4. A cover engaging portion 6 is formed at the upper end of the side wall 5. The cover 3 comprises a top plate 7 and a high side wall 8 rising upright from the periphery of the top plate 7. The high side wall 8 has a height about twice that of the main body 2. On the lower end of the high side wall 8 there is formed a main body engaging portion 9 which comes into engagement as close as possible with the cover engaging portion 6 on the upper end of the side wall of the main body 2. In this embodiment shown in the drawings, the engaging portions 6 and 9 are thread-engaged with the main body 2 and the cover 3 respectively. Furthermore, they may be pressed-fit or an excess bayonet connecting means is optional.

A projected edge 11 is formed on the periphery of the cover 3. The projected edge 11 engages with a stepped portion 10 formed on the periphery of the bottom 4 of the main body 2 so that a plurality of the vessels can be stacked without sliding. The inside peripheral surface 11a of the projected edge 11 is tapered to diverge upward.

Figure 2A:
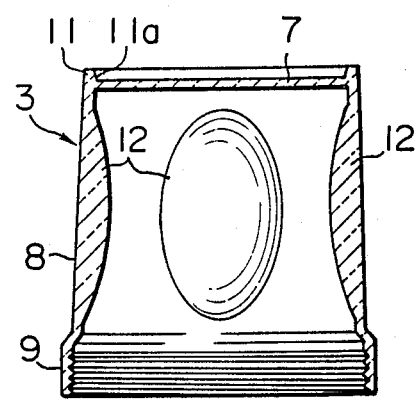
FIGS. 2(A) and (B) are longitudinal sectional views of the main body and the cover taken along the line II—II of FIG. 1.
Figure 2B:
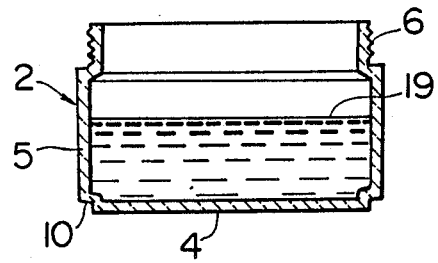

On the side wall 8 of the cover 3 there is provided a lens 12 for magnifying the image in the interior of the main body 2. The lens 12 is exemplified in FIGS. 2 to 7. In the embodiment of FIG. 2, a plurality of convex lenses 12 are formed integrally with the side wall 8 of the cover 3 when the cover 3 is formed. For the molding of the cover 3, a longitudinally split mold is used. The number of the convex lenses 12 is suitably selected depending on the size of the vessel; four of which are arranged circumferentially, three of which are arranged equidistantly from each other as shown in a horizontal sectional view of FIG. 3, and two of which are arranged at symmetrical positions, or others.

Figure 4:
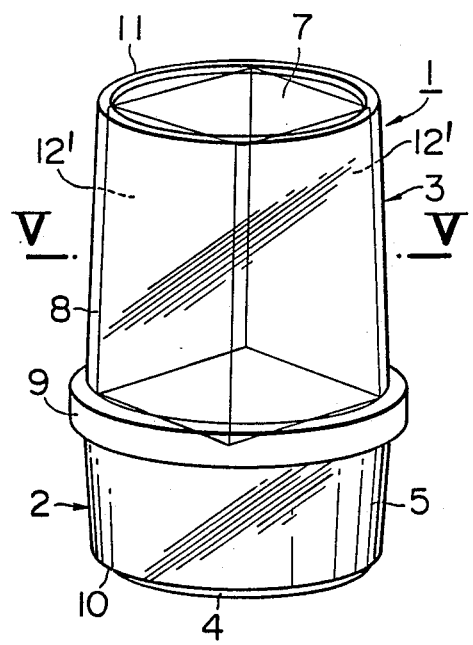
FIG. 4 is a perspective view of another embodiment.
Figure 5:
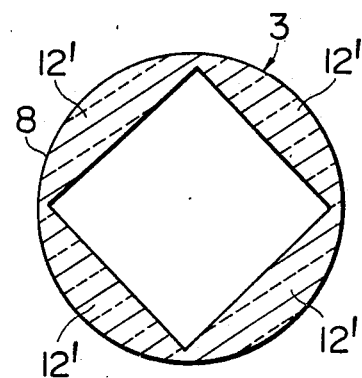
FIG. 5 is a horizontal sectional view taken along the line V—V of FIG. 4.

The embodiment of FIGS. 4 and 5 has plane convex lenses 12' having the convex surfaces which are provided with the arcuate outside peripheral surface of the side wall 8 of the cover 3 and having the inside surfaces of the convex surfaces formed in plane surfaces. In this engaged. It is possible to form recesses suitably in the projected edge 11 for the drainage of water from the top plate 7.

A cylindrical ventilation plug 18 is filled in the plug receiving cavity 13 as closely as possible. The ventilation plug 18 is made of a material which does not shrink even when the plug 18 is subjected to not only dry pasteurization but also to wet (vapor) pasteurization by the autoclave. The material is nonwoven fabric of, e.g., thermoadhering fiber comprising as raw materials polypropylene and polyethylene parallelly compounded. The material is rolled, folded, or compressed with the longitudinal axis in the direction of orientation of the fibers, and wrapped with Japanese paper or other material into a cylindrical shape having a thickness of 8-9Φ and a length of around 11 m/m.

In FIG. 2, reference numeral 19 represents a medium. The operation of the above-described embodiments will be explained below. A medium 19 is put in the main body 2, and tissue pieces of a plant, or others are placed in the medium. The main body 2 is shallow, and the medium 19 is located near the open top of the main body 2. The manipulation of placing the tissue pieces on the medium is easy, and the tissue pieces can be laid easily in the same direction. Then the main body engaging portion 9 is screwed onto the cover engaging portion 6 of the main embodiment, four plane convex lenses 12' are formed by molding. The number of the plane convex lenses is also optional in this embodiment; a couple of the lenses may be arranged at symmetrical positions. Punching may be used for this embodiment.

Figure 6:
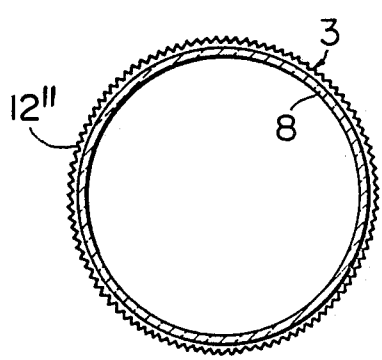
FIGS. 6 and 7 are views of embodiments corresponding to FIG. 5 in which Fresnel lens is used.
Figure 7:
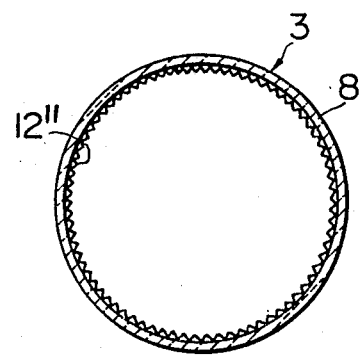

In the embodiments of FIGS. 6 and 7 Fresnel lenses 12" are used. In the embodiment of FIG. 6, a Fresnel lens 12" in the form of a sheet is wound on and adhered to the outside surface of the side wall 18 of the cover 3. In the embodiment of FIG. 7, the sheet is adhered to the inside surface of the side wall 8 of the cover 3 along thereto. The Fresnel lens may be formed integrally with a part of the outside surface of the side wall 8 or the inside surface thereof when the cover 3 is formed by using a split mold.

It is preferable that the lenses 12, 12', 12" have a magnification, $X=b/a$, of $1.3<X<2.0$ when a distance to an object to be observed is represented by (a), a distance to an image (b), the focal length (f) and $a<f$ so as to gain virtual images.

Figure 3:
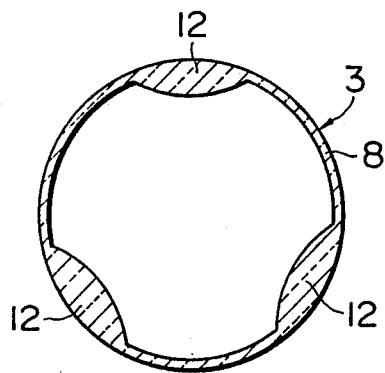
FIG. 3 is a horizontal sectional view of the embodiment in which three lenses are provided on the cover.
Figure 8:
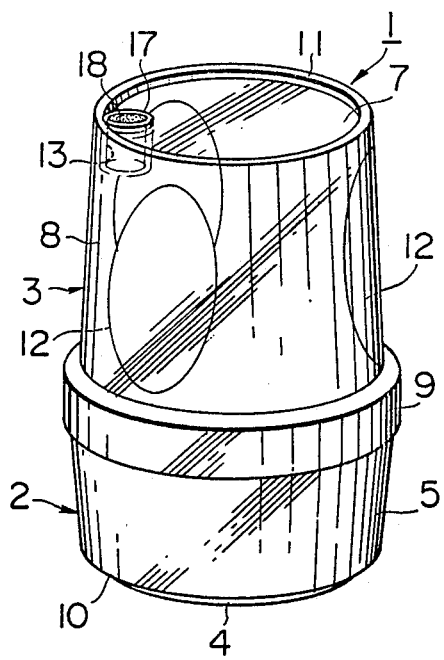
FIG. 8 is a perspective view of still another embodiment.
Figure 9:
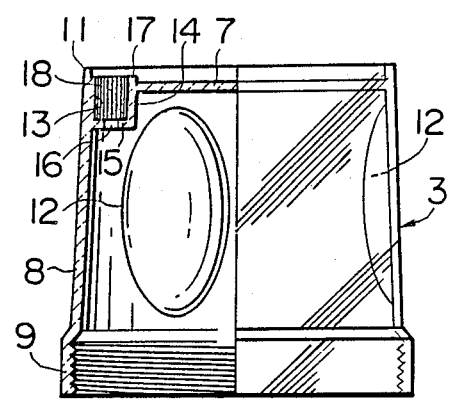
FIG. 9 is a longitudinal half-sectional view of the cover.
Figure 10:
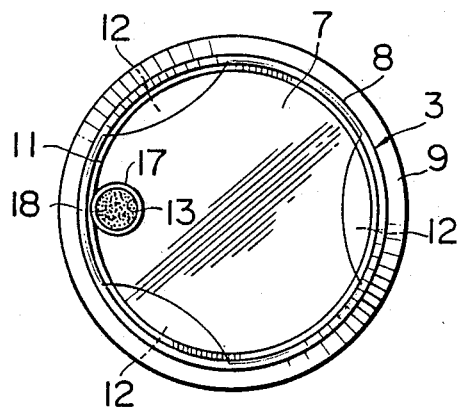
FIG. 10 is a plan view of FIG. 9.

Around the periphery of the open top of the plug receiving cavity 13, there is provided a projected wall 17 lower than the projected edge 11 on the periphery of the top plate 7. The projected wall 17 has a height which allows the projected wall 17 to be positioned short of the bottom 4 of the main body 2 when the vessel is stacked on another vessel with the projected edge 11 body 2, and the longitudinally cylindrical culture vessels 1 shown in FIGS. 1, 3 and 8 are prepared.

Figure 11:
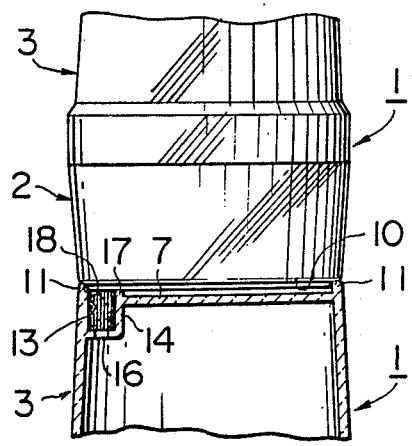
FIG. 11 is a view explaining the culture vessels in their stacked condition.
Figure 12A:
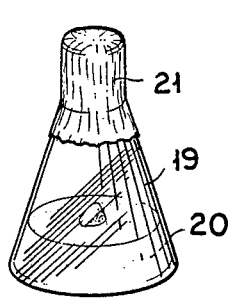
FIG. 12 is a perspective view of the conventional culture vessel in the form of a glass triangular flask, FIG. 12(A) showing the plug of aluminium foil, FIG. 12(B) showing the cotton plug, and FIG. 12(C) showing the silicone plug.
Figure 12B:
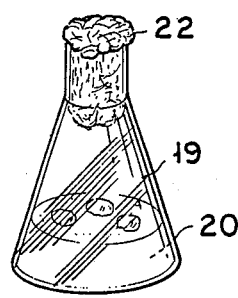
Figure 12C:
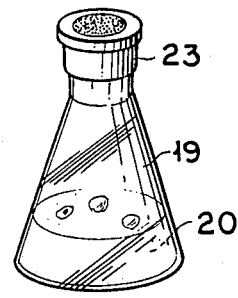
Figure 13:
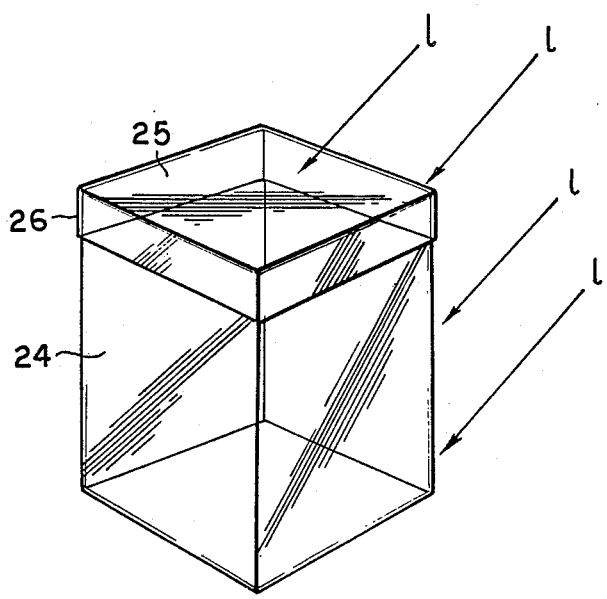
FIG. 13 is a perspective view of the conventional plastic culture vessel.

As shown in FIG. 11, the culture vessels 1 which are empty or loaded with a substance to be cultivated are stacked with the stepped portion 10 on the periphery of the bottom of the upper main body 2 of the upper culture vessel 1 engaged with the projected edge 11 on the periphery of the cover of the lower culture vessel 1. The culture vessels 1 can be firmly stacked in order without sliding.

The culture vessel 1 having the lenses 12, 12', 12" on the cover 3 in this manner permits light to be transmitted well. Moreover, the engaging portion 9 between the cover 3 and the main body 2 is positioned low near the main body, which permits direct light to be poured to the medium and the whole culture vessel without any interruption. When the interior of the culture vessel is observed, the substance being cultivated in the culture vessel can be observed in a magnified image by the lenses 12, 12', 12" provided on the side wall of the cover 3. Even when the culture vessels 1 are stacked in a number of layers, the interiors of the stacked culture vessels can be easily observed in a magnified image, and the growing states can be determined accurately.

When a cultured substance which has grown in the culture vessel 1 for a certain period of time is taken out of the main body 2 after the cover 3 is taken off the of a transparent plastic material having good light transmission, the main body is shallow, the cover is deep, and the main body and the cover can be connected. This structure facilitates pouring a medium into the main body, planting various substances to be cultivated on the medium, and transplanting the cultured substance into other culture vessels, simply by taking the cover off the main body. The cover, which has also good light transmission, permits direct light to illuminate the whole culture vessel. Moreover, the interior of the culture vessel can be easily observed.

When the main body and the cover are connected, the connection is located near the substance being cultured therein. Accordingly the culture vessel has improved ventilated conditions; $CO_2$ is absorbed rapidly. This results in good effects on the growth of the plant in the culture vessel. The lenses on the side wall of the cover make it possible to observe changes of the state of the substance being cultivated in the main body in a magnified image, and thus a state of the interior of the main body can be accurately determined. Even when the culture vessels are stacked in a plurality of layers, the interiors of the staked culture vessels can be efficiently observed owing to the lenses on the side walls of the covers, and without taking out the respective culture vessels out of the layers. main body 2, the cultured substance can be taken out of the main body 2 without being damaged since the cultured substance is located near the top of the main body 2.

The interior of the culture vessel 1 according to the embodiment of FIG. 8 is placed in a ventilated condition with the outside air supplied through the ventilation plug 18 filled in the plug receiving cavity 13 of the cover and the ventilation hole 16 in the bottom 15 of the plug receiving cavity 13. This culture vessel is usable for aerobic culture.

The ventilation plug 18 used in the cover 3 of the culture vessel 1 has good heat resistance and does not shrink due to absorbed water. Accordingly it neither loses the ventilating function, nor becomes loose or drops off. Furthermore, there is no risk that the ventilation plug 18 will collapse when the culture vessels are stacked, since the upper exposed portion of the ventilation plug 18 is protected by the projected wall 17 on the periphery of the open top of the plug receiving cavity 13. Furthermore, the projected wall 17 keeps the water on the cover 3 from flowing into the plug receiving cavity 13 and into the culture vessel 1.

In the embodiments shown in the drawings, the main body 2 and the cover 3 are of circular section but may be of polygonal section.

As described above, in the culture vessel according to this invention, the main body and the cover are made The plug receiving cavity which is formed in the top plate of the cover of the culture vessel, and the ventilation plug is filled in the cavity. The plug has a cylindrical shape and is made of a material (e.g., nonwoven fabric) having good heat resistance and free from shrinkage due to absorbed water, and is formed with its longitudinal axis in the direction of orientation of the fibers. As a result, the plug assures the ventilation in the interior of the culture vessel and, at the same time, allows the culture vessel to be subjected to the vapor pasteurization.

Furthermore, the projected wall, which is provided on the periphery of the open top of the plug receiving cavity, holds back the water resting on the top plate of the cover, and the intrusion of the water into the culture vessel is prevented. Accordingly the contamination of the plant tissues on the main body is prevented, while the culture vessels can be stacked without any trouble. In addition, it is not necessary that the culture vessel be faced in a certain direction when it is handled. This makes the culture vessel usable in future automated culturing with robots and automatic transplantation.

The use of nonwoven fabric as the material of the ventilation plug, and the cylindrically shaped plug formed with the longitudinal axis in the direction of orientation of the fibers make the plug inexpensive (below 1/10) compared with the conventional ventilation plugs of silicone and Ohme cotton (one kind of Japanese cotton). Moreover, the ventilation plug does not substantially shrink even when it is subjected to the vapor pasteurization. The nonwoven fabric is most suitable as a material of the ventilation plug used in this invention. The length of the ventilation plug is the depth of the plug receiving cavity plus a height of the projected wall.

What is claimed is:

1. A plant culture vessel having a main body which is provided with an open top and a cover for closing the open top of the main body, wherein said main body and said cover are made of a thin plastics material having light transmission and resistance properties, said main body has a bottom and a low side wall for accommodating a medium, said low side wall has a cover engaging portion formed on an upper end thereof, said cover has a top plate and an upright high side wall, said high side wall has a main body engaging portion, on a lower end thereof, meshable with said cover engaging portion of the main body, and a plurality of magnifying lenses, formed integrally with said high side wall, having a focal length usable for observing the interior of the vessel in a magnified image are provided circumferentially about the high side wall of said cover.

2. A plant culture vessel according to claim 1, wherein on the top plate of said cover there is provided a plug receiving cavity with a ventilation hole, and said plug receiving cavity is filled with a ventilation plug made of a material which is unshrinkable with respect to wet pasteurization treatment.

3. A plant culture vessel according to claim 2, wherein the top plate of said cover has a projected edge for engaging with the bottom of said main body to make the vessel stackable formed at the upper end of the periphery thereof, and said plug receiving cavity has a projected wall lower than the projected edge formed on the periphery of the top opening of said plug receiving cavity.

4. A plant culture vessel according to claim 1, wherein said lenses are of elliptical shape and are arranged equidistantly on the high side wall along the longitudinal upright axis.

5. A plant culture vessel according to claim 1, wherein said lenses are Fresnel lenses.

6. A plant culture vessel according to claim 1, wherein the height of the high side wall is twice the height of the low side wall.

7. A culture vessel having a main body which is provided with an open top and a cover for closing the open top of the main body, wherein said main body and said cover are made of a thin plastics material having light transmission and heat resistance properties, said main body has a bottom and a low side wall for accommodating a medium, said low side wall has a cover engaging portion formed on an upper end thereof, said cover has a top plate nd an upright high side wall, said high side wall has a main body engaging portion, on a lower end thereof, meshable with said cover engaging portion of the main body, and at least one magnifying lens, formed integrally with said high side wall, having a focal length usable for observing the interior of the vessel in a magnified image.

* * * * *